US008772184B2

(12) United States Patent
Farrugia et al.

(10) Patent No.: US 8,772,184 B2
(45) Date of Patent: Jul. 8, 2014

(54) REVERSIBLE COLOR-CHANGING SANITIZER-INDICATING NONWOVEN WIPE

(75) Inventors: Darren J. Farrugia, Pasadena, CA (US); Lesley J. Ward, Manasquan, NJ (US); Veronica R. Reichert, Wauconda, IL (US)

(73) Assignee: Illinois Tool Works Inc., Glenview, IL (US)

(*) Notice: Subject to any disclaimer, the term of this patent is extended or adjusted under 35 U.S.C. 154(b) by 530 days.

(21) Appl. No.: 12/702,138

(22) Filed: Feb. 8, 2010

(65) Prior Publication Data

US 2010/0247371 A1    Sep. 30, 2010

Related U.S. Application Data

(60) Provisional application No. 61/211,505, filed on Mar. 31, 2009.

(51) Int. Cl.
*C11D 3/48* (2006.01)
(52) U.S. Cl.
USPC ............................................. 442/59; 442/123
(58) Field of Classification Search
USPC ............................................. 442/59, 123
See application file for complete search history.

(56) References Cited

U.S. PATENT DOCUMENTS

| 4,311,479 A | 1/1982 | Fenn et al. |
| 4,678,704 A | 7/1987 | Fellows |
| 5,503,076 A | 4/1996 | Yeo |
| 5,580,578 A * | 12/1996 | Oshlack et al. ............... 424/468 |
| 5,948,605 A | 9/1999 | Wang et al. |
| 5,962,001 A * | 10/1999 | Rose et al. .................... 424/404 |
| 6,017,869 A | 1/2000 | Lu et al. |
| 6,312,484 B1 | 11/2001 | Chou et al. |
| 6,794,318 B2 | 9/2004 | Anderson et al. |
| 7,314,752 B2 | 1/2008 | Kritzman et al. |
| 2001/0031595 A1 | 10/2001 | Anderson et al. |
| 2002/0108640 A1 * | 8/2002 | Barger et al. ................... 134/26 |
| 2004/0038848 A1 | 2/2004 | Kritzler |
| 2004/0209539 A1 | 10/2004 | Confalone et al. |

(Continued)

FOREIGN PATENT DOCUMENTS

| CN | 1429085 A | 7/2003 |
| CN | 1625379 A | 6/2005 |

(Continued)

OTHER PUBLICATIONS

H.Starp et al., "Novel teststrip with increased accuracy," Fresenius J Anal Chem (2000), 368, pp. 203-207.

(Continued)

*Primary Examiner* — Peter Y Choi
(74) *Attorney, Agent, or Firm* — Pauley Petersen & Erickson

(57) ABSTRACT

A nonwoven wipe having a reversible sanitizer indicator for multiple uses and recharges is provided. The nonwoven wipe includes a cloth-like nonwoven fabric coated with a reversible color-changing ink formulation. During use, the nonwoven wipe is impregnated with a quaternary ammonium compound-based sanitizer. When the level of free quaternary ammonium compound falls below a threshold level, the color-changing ink formulation changes from a first color to a second color, indicating the need to recharge the wipe. When the nonwoven wipe is recharged with sanitizer solution, the color-changing ink formulation changes back to the first color.

18 Claims, 1 Drawing Sheet

(56) References Cited

U.S. PATENT DOCUMENTS

| | | |
|---|---|---|
| 2006/0293205 A1 | 12/2006 | Chung |
| 2007/0238190 A1 | 10/2007 | Klei et al. |
| 2007/0238831 A1 | 10/2007 | Klei et al. |
| 2012/0093736 A1 | 4/2012 | Jelonek et al. |
| 2013/0104325 A1 | 5/2013 | Farrugia et al. |

FOREIGN PATENT DOCUMENTS

| | | |
|---|---|---|
| CN | 1878835 A | 12/2006 |
| CN | 101330896 A | 12/2008 |
| JP | 60-178362 A | 9/1985 |
| WO | WO 01/87132 A1 | 11/2001 |
| WO | WO 2010/079098 A1 | 7/2010 |

OTHER PUBLICATIONS

T. Werner et al., "Ammonia-sensitive Polymer Matrix Employing Immobilized Indicator Ion Pairs," Analyst, Jun. 1995, vol. 120, pp. 1627-1631.

W. Wroblewski et al., "Cellulose based bulk pH optomembranes," 1998 Elsevier Science S.A., B 48, pp. 471-475.

Co-pending U.S. Appl. No. 13/720,154, filed Dec. 19, 2012; inventors Darren J. Farrugia et al.; title Reversible Color-Changing Sanitizer-Indicating Wipe.

* cited by examiner

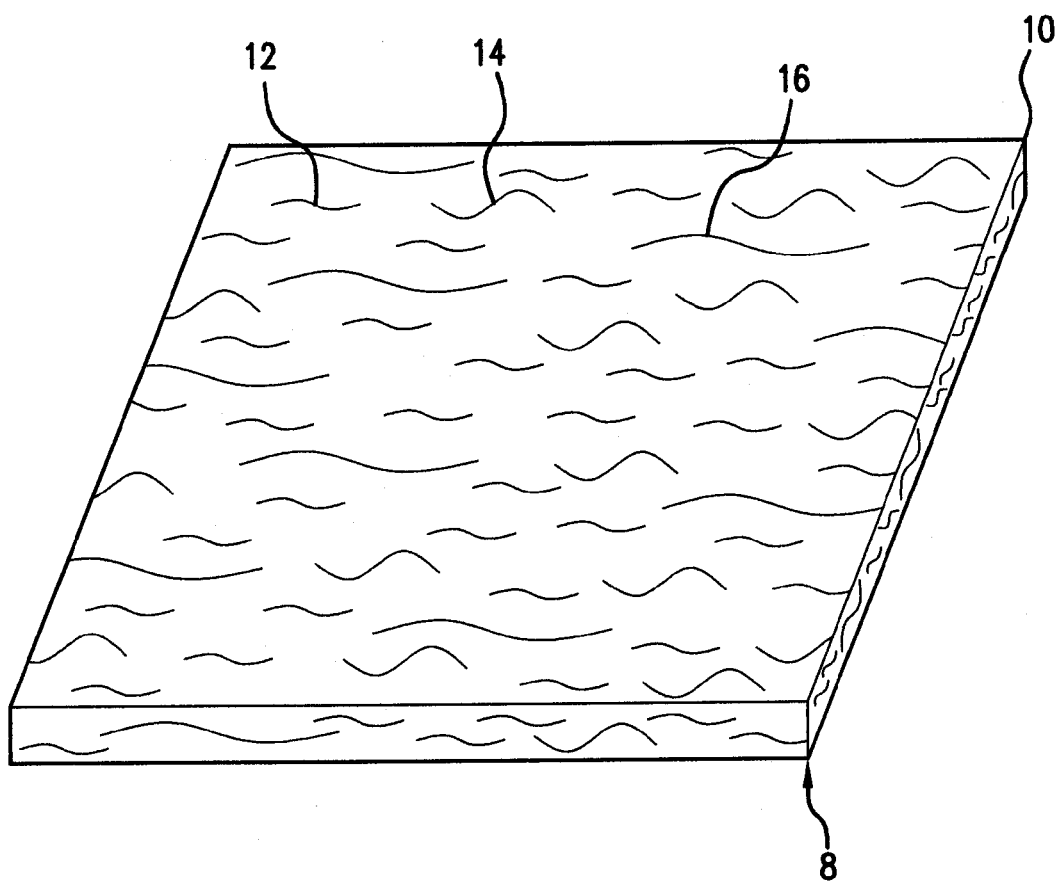

REVERSIBLE COLOR-CHANGING SANITIZER-INDICATING NONWOVEN WIPE

CROSS REFERENCE TO RELATED APPLICATION

This application claims the benefit of U.S. Provisional Application No. 61/211,505 filed on 31 Mar. 2009. This Provisional Application is hereby incorporated by reference herein in its entirety and is made a part hereof, including but not limited to those portions which specifically appear hereinafter.

FIELD OF THE INVENTION

The present invention is directed to a nonwoven wipe whose color changes from a first color to a second color when the concentration of sanitizer falls below a threshold level, and changes from the second color back to the first color when the concentration of sanitizer is again raised above the threshold level, for repeated cycles of use.

BACKGROUND OF THE INVENTION

Fabric wipes having color indicators are disclosed in U.S. Pat. No. 4,311,479, issued to Fenn et al., and in U.S. Pat. No. 4,678,704, issued to Fellows. Fenn et al. discloses a cloth impregnated with an antimicrobial composition that is activated upon contact with a liquid such as water, and is ionically bonded to the cloth. Small portions of the impregnated cloth are dyed with an indicator dye which bonds preferentially to the antimicrobial composition so that when the antimicrobial composition is exhausted, the dye will disappear from the cloth.

Fellows discloses an impregnated fabric material having an active cationic impregnant bonded to its fabric substrate. An anionic indicator dye in combination with a further cationic component is also bonded to the substrate. The dye bonds to the further cationic component more readily than to the substrate and the further cationic component competes with the impregnant for bonding to the dye. In the case of a wiping cloth, when the dye has been removed to indicate exhaustion of the active component, enough active component remains on the cloth to provide a safety margin.

While these and similar prior art fabrics had color indicators to indicate the dissipation of impregnant, the indicators only worked once, and only changed color once. If the fabric was then recharged with impregnant, such as by dipping it into a bucket, the original color would not return and the indicator function would not return.

There is a need or desire for fabrics impregnated with cleansing solutions, disinfectants and the like which can be recharged multiple times for multiple uses, and which indicate each time when the level of cleansing solution or disinfectant becomes low.

SUMMARY OF THE INVENTION

The present invention is directed to a nonwoven wipe having a reversible color-changing sanitizer indicator for multiple uses and recharges. The nonwoven wipe can be used to wipe down tables and countertops, for example, until the concentration of sanitizer in the wipe falls below a threshold concentration. At that point, the color of the nonwoven wipe changes from a first color to a second color. The nonwoven wipe can then be recharged, for example by immersing it in a bucket of sanitizer solution. The recharged nonwoven wipe then changes back to the first color, and can be used until the concentration of sanitizer falls to the threshold concentration and the color again changes to the second color. The nonwoven wipe is recharged again, and the cycle is repeated until the nonwoven wipe becomes exhausted due to soiling or damage, or the cleaning task is completed.

The nonwoven wipe includes a cloth-like nonwoven fabric formed, at least in part, of absorbent nonwoven fibers formed from cellulose or another suitable material. The absorbent fibers can be formed to rayon. The nonwoven fibers can be used alone or in combination with reinforcing nonwoven fibers, which need not be absorbent. The structural fibers can be formed of polyester or another suitable material.

The cloth-like nonwoven fabric is coated with a reversible color-changing ink formulation that durably binds itself to the nonwoven fabric, and remains bound during repeated use cycles. The reversible color-changing ink formulation includes about 10-50% by weight of a polymer binder, about 10-50% by weight of a plasticizer, about 10-50% by weight of a wetting agent, about 0-10% by weight of an ionic stabilizer, and about 1-10% by weight of an anionic indicator compound, based on dry weight of the ink formulation. The ingredients of the ink are dissolved in a volatile organic solvent for application to the cloth-like nonwoven fabric. When fully dried, the ink does not leach or otherwise escape from the nonwoven wipe, and can reversibly change color to indicate the relative concentration of sanitizer in the nonwoven wipe.

The nonwoven wipe is impregnated with a sanitizer, suitably one that is based on a quaternary ammonium compound. The nonwoven wipe may be provided with the sanitizer already impregnated. Alternatively, the nonwoven wipe may be provided without sanitizer, and may be impregnated with sanitizer by the user. In a preferred embodiment, the desired minimum concentration of quaternary ammonium compound in the nonwoven wipe (which causes color change) may range from about 180 ppm to about 250 ppm, based on the dry weight of the nonwoven wipe. The nonwoven wipe is impregnated with a higher amount of quaternary ammonium compound, as explained below. When the concentration of quaternary ammonium compound falls to the threshold level during use, the resulting color change indicates the need to recharge. The quaternary ammonium compound is often provided in an aqueous solution, and can be applied by dipping the nonwoven wipe in a bucket containing the sanitizer solution.

By reversibly changing color during use, the nonwoven wipe provides a reliable indication of when it needs to be recharged during use, due to depletion of the sanitizer. By maintaining proper sanitizer concentration, the nonwoven wipe can be used for as long as it is needed to complete the task at hand, or until the wipe becomes damaged or heavily soiled.

With the foregoing in mind, it is a feature and advantage of the invention to provide a nonwoven wipe having a reversible color-changing sanitizer indicator, which nonwoven wipe can be recharged and used several times while providing a reliable indication of sanitizer concentration.

It is also a feature and advantage of the invention to provide a nonwoven wipe having extended use life due to the presence of a durable indicator which repeatedly and reversibly indicates changes in sanitizer concentration in the nonwoven wipe.

BRIEF DESCRIPTION OF THE DRAWINGS

FIG. 1 is a perspective view of a nonwoven wipe according to the invention.

DETAILED DESCRIPTION OF THE INVENTION

Referring to FIG. 1, a reversible color-changing sanitizer indicating nonwoven wipe 8 of the invention includes a cloth-like nonwoven fabric 10 including a plurality of nonwoven fibers 12. The nonwoven fibers 12 include absorbent nonwoven fibers 14 and may optionally include reinforcing nonwoven fibers 16, which may be absorbent or nonabsorbent. The absorbent nonwoven fibers 14 may be formed from cellulose or another suitable absorbent material. Suitable cellulose fibers include without limitation fibers formed from wood, cotton, silk, straw, hay, and other plants. Rayon fibers are particularly suitable for the absorbent nonwoven fibers 14. Rayon fibers are textile filaments made from cotton linters, wood chips or other cellulose by treating them with caustic soda and carbon disulfide, and passing the resulting viscose solution through spinnerets.

When used, the reinforcing nonwoven fibers 16 may be formed from any strong, flexible polymeric material. Suitable polymeric materials include without limitation polyester, polypropylene, high density polyethylene, linear low density polyethylene, polyamides, polytetrafluoroethylene, and combinations thereof. The cloth-like nonwoven fabric 10, specifically the nonwoven fibers 12, may include about 50-100% by weight of the absorbent nonwoven fibers 14 and about 0-50% by weight of the reinforcing nonwoven fibers 16, suitably about 55-90% by weight of the absorbent nonwoven fibers 14 and about 10-45% by weight of the reinforcing nonwoven fibers 16, or about 60-80% by weight of the absorbent nonwoven fibers 14 and about 20-40% by weight of the reinforcing nonwoven fibers 16.

In accordance with the invention, the cloth-like nonwoven fabric 10 is coated with a reversible color-changing ink formation that is sensitive to the concentration of quaternary ammonium compound in the nonwoven wipe 8. On a dry weight basis, the color-changing ink formulation includes about 10-50% by weight of a polymer binder, suitably about 20-45% by weight, or about 30-40% by weight. The polymer binder helps bond the nonwoven fibers 12 of the fabric 10 together, and also forms a durable bond between the nonwoven fabric 10 and the remaining ingredients of the color changing ink formulation. The relatively high amount and bond strength of the binder polymer help ensure that the reversible color-changing ingredients of the ink formulation will remain intact and functional for the useful life of the nonwoven wipe 8.

Suitable polymeric binder compounds include without limitation cellulose acetate and cellulose acetate derivatives. One suitable polymeric binder is cellulose acetate having a number average molecular weight of about 30,000, sold by Aldrich Chemical Co. Other suitable polymeric binders are cellulose acetate butyrates having number average molecular weights of about 16,000, 20,000 and 30,000 sold by Eastman Chemical Co. under the trade names CAB 551-0.01, CAB 553-0.4 and CAB 551-0.2, respectively. Other suitable polymeric binders include without limitation cellulose acetate propionate, polymers of carboxymethyl cellulose, polymers of ethyl cellulose, polymers of nitrocellulose, and combinations thereof.

The reversible color-changing ink formulation also includes about 10-50% by weight plasticizer on a dry weight basis, suitably about 15-40% by weight, or about 20-30% by weight. The plasticizer helps maintain the flexibility of the nonwoven wipe 8 with the color changing ink formulation applied, i.e., by softening the color-changing ink formulation so that it does not stiffen the nonwoven wipe 8. Suitable plasticizers include without limitation dibutyl phthalate and triethyl citrate sold by Aldrich Chemical Co. Other suitable plasticizers include without limitation bis-(2-butoxyethyl) adipate, bis-(2-ethylhexyl) sebacate, diethyl phthalate, and combinations thereof.

The reversible color-changing ink formulation also includes about 10-50% by weight of a wetting agent on a dry weight basis, suitably about 15-40% by weight, or about 20-35% by weight. The wetting agent causes the color-changing ink formulation to spread, cover and (to an extent) envelop the nonwoven fibers 12 of the fabric 10, resulting in more durable bonding between the color-changing ink formulation and the nonwoven fabric 10. Suitable wetting agents include without limitation ethylene glycol and 2-ethoxy ethanol sold by Aldrich Chemical Co. Other suitable wetting agents include without limitation triethylene glycol, sorbitol, and combinations thereof.

The reversible color-changing ink formulation may include about 0-5% by weight, suitably about 0-3% by weight of an ionic stabilizer, based on the dry weight of the ink formulation. When used, the ionic stabilizer may be a quaternary ammonium compound, and may be chemically similar or identical to the quaternary ammonium compound used in the sanitizer solution that is later impregnated into the nonwoven wipe 8. When used, the concentration of ionic stabilizer should not be so great as to prevent the color-changing ink from responding to the concentration of quaternary ammonium compound resulting from the sanitizer solution in the nonwoven wipe. Suitable ionic stabilizers include without limitation di (long chain alkyl) dimethyl ammonium chlorides; N-methyl-N,N-bis(long chain alkanoyl oxyethyl)-N-(2-hydroxymethyl) ammonium methylsulfates; vinylbenzyl dimethylcocoammonium chlorides; and methyl trioctyl ammonium chlorides. One suitable anionic stabilizer is STEPANQUAT®2125M-P40, available from Stepan Company. This product is a mixture of about 50% by weight N-alkyl (60% C14, 30% C16, 5% C12 and 5% C18) dimethyl benzyl ammonium chlorides and about 50% by weight N-alkyl (68% C12 and 32% C14) dimethyl ethyl benzyl ammonium chlorides.

The reversible color-changing ink formulation includes about 1-10% by weight of an anionic indicator compound on a dry weight basis, suitably about 1.5-7% by weight, or about 2-4% by weight. The amount of anionic indicator is small relative to the amount of binder polymer, thus ensuring a durable, permanent bond to the nonwoven fabric 10. The anionic indicator reversibly changes color when the amount of quaternary ammonium compound in the sanitizing solution surpasses a predetermined level in either direction. The anionic indicator causes the ink to change from a first color to a second color during use of the nonwoven wipe, when the concentration of quaternary ammonium compound in the nonwoven wipe falls below a selected level. Then, when the nonwoven wipe is recharged with the quaternary ammonium compound based sanitizer, the anionic indicator causes the ink to change from the second color back to the first color.

The specific type of anionic indicator used may depend on the desired threshold concentration of anionic indicator that triggers the color change. Different anionic indicators trigger color changes at different concentrations of quaternary ammonium compounds. More than one anionic indicator may also be used, if it is desired to indicate two or more color changes at two or more different concentrations of quaternary ammonium compounds. The anionic indicator(s) may include without limitation one or a plurality of compounds selected from bromothymol blue, thymol blue, m-cresol purple, xylenol blue, xylenol orange, phenol red, and combinations thereof.

The reversible color-changing ink formulation may also include about 1-25% by weight, suitably about 10-20% by weight of a particulate inorganic filler. It has been found that inclusion of a filler helps improve the intensity of the color change, so that the color change becomes more apparent and visible. Suitable particulate fillers include without limitation silicon dioxide, titanium dioxide, calcium carbonate, and combinations thereof. One particularly suitable filler is amorphous silica (amorphous silicon dioxide) available from W.R. Grace & Co. under the trade name SYLOID® C 803.

The ink ingredients can be mixed together in a volatile organic solvent in an amount of about 15-50% by weight total ink ingredients based on the combined weight of the ink ingredients and solvent. Suitable volatile organic solvents which also dissolve the ink ingredients include without limitation n-propyl acetate and volatile ketones, for example acetone, methylethyl ketone, toluene, tetrahydrofuran, ethyl acetate, and combinations thereof. The color-changing ink solution can be applied to the nonwoven fabric 10 by dipping, dripping, immersion, spray coating, brush coating, roll coating, printing, or any suitable technique. The coated nonwoven fabric 10 can then be dried in the presence of heat and/or vacuum to remove the volatile organic solvent, leaving the color-changing ink composition firmly bonded to the nonwoven fabric 10. Drying temperatures of about 40° C. to about 60° C. are generally sufficient. The drying times may range from several minutes to several hours depending on the particular composition, structure and basis weight of the nonwoven fabric 10, and on the specific composition of the color-changing ink composition.

After drying, the reversible color-changing ink composition should constitute about 1.0-10% by weight, suitably about 3-5% by weight of the nonwoven wipe 8. These amounts are based on the weight of the dry nonwoven wipe 8, before it is charged with a quaternary ammonium compound-based sanitizer solution.

During use, the nonwoven wipe 8 is typically charged with quaternary ammonium compound-based sanitizer solution by dipping or immersing the nonwoven wipe 8 in a cleaning bucket that contains the sanitizer solution, typically diluted with water. The nonwoven wipe 8 may also be provided as a precharged wipe which is already impregnated with quaternary ammonium compound-based sanitizer solution. One suitable quaternary ammonium compound-based sanitizer is the above-described STEPANQUAT® 2125M-P40, available from Stepan Company. Again, this product is a mixture of about 50% by weight N-alkyl (60% C14, 30% C16, 5% C12 and 5% C18) dimethyl benzyl ammonium chlorides and about 50% by weight N-alkyl (68% C12 and 32% C14) dimethyl ethyl benzyl ammonium chlorides. The product is available as a powder. For use as a sanitizing solution, the powder can be added to water in an amount which results in an aqueous solution having a quaternary ammonium compound concentration of about 0.195-0.225% by weight.

The aqueous sanitizer solution is applied to the nonwoven wipe 8, as noted above, by dipping or immersing the nonwoven wipe 8 in the sanitizer solution. The amount of sanitizer solution absorbed by the nonwoven wipe 8 depends on the structural characteristics, basis weight and absorbent characteristics of the nonwoven wipe 8. As explained above, the sanitizer solution may contain about 180 to about 400 ppm, suitably about 180 to about 250 ppm of the quaternary ammonium compound. When fully charged, the nonwoven wipe 8 will typically contain about 150-350% by weight, suitably about 250-300% by weight of the aqueous sanitizer solution based on the dry weight of the nonwoven wipe 8. As explained above, the sanitizer solution may contain about 180 to about 400 ppm, suitably about 180 to about 250 ppm of the quaternary ammonium compound. The free quaternary ammonium compound content of the nonwoven wipe 8, based on the dry weight of the nonwoven wipe 8, is suitably about 300 to about 1200 ppm, or about 500 ppm to about 1000 ppm. The term "free quaternary ammonium component content" refers to the amount of quaternary ammonium compound contributed by the sanitizer solution, and does not include any quaternary ammonium compound contained in the color-changing ink composition as an ionic stabilizer.

To determine a threshold concentration of free quaternary ammonium compound in the nonwoven wipe that causes a particular applied ink composition to change from a first color to a second color during use, the following procedure can be followed. First, the weight "D" of the dry nonwoven wipe 8 with applied ink composition is measured. Then, the nonwoven wipe 8 is impregnated with aqueous sanitizer solution and weighed, to determine the fully charged weight "C". The amount "Q" of quaternary ammonium compound in the fully charged nonwoven wipe 8 is determined by multiplying the weight ratio "R" of quaternary ammonium compound in the aqueous cleaning solution by the difference between C and D, according to the following equation:

$$Q = R(C-D)$$

The fully charged concentration "P" (in parts per million) of quaternary ammonium compound in the nonwoven wipe 8, based on the dry weight of the nonwoven wipe 8, is therefore $(Q/D) \times 10^6$.

To determine the threshold concentration of quaternary compound that triggers a color change during use, simply wipe the nonwoven wipe 8 across a table or countertop until the color begins to change from the first color to the second color, and weigh the nonwoven wipe 8 again to determine the depleted weight "L." The threshold concentration T (in parts per million) can be determined from the following equation:

$$T = P\frac{(L-D)}{(C-D)}$$

By following the foregoing procedure, different ink compositions can be tested for a particular nonwoven wipe 8 to develop an ink composition which changes color at a desired threshold concentration T. In most instances, the desired threshold concentration T for a nonwoven wipe 8 is about 180-250 ppm, suitably about 190-220 ppm. When the concentration of quaternary ammonium compound in the nonwoven wipe 8 falls below the threshold level, the nonwoven wipe 8 becomes less effective for sanitizing applications, and it becomes important to recharge the nonwoven wipe 8 with sanitizer solution.

Once the threshold concentration T has been determined for a particular ink composition, a much simpler procedure can be used to determine the relative sensitivity of different ink compositions, i.e. whether different ink compositions will change color at higher or lower levels of quaternary ammonium compound. To determine the relative sensitivity of different ink compositions, sanitizer solutions containing several different concentrations of quaternary ammonium compound can be prepared in separate buckets or containers. For example, solutions containing quaternary ammonium compounds at 0 ppm, 50 ppm, 125 ppm, 250 ppm, 500 ppm and 1000 ppm can be prepared. Then, nonwoven wipes coated with different color-changing ink compositions can each be dipped sequentially into the sanitizer solutions, beginning with the lowest concentrations, to determine the concentration of quaternary ammonium compound that triggers a color change. While this simpler procedure can be used to determine if one ink changes color at a higher or lower quaternary ammonium content relative to another ink, it will not determine the threshold concentration T of quaternary ammonium compound in a nonwoven wipe 8.

It is also within the scope of the invention to provide a method of cleaning a surface. The method includes the steps of providing a nonwoven wipe including a nonwoven fabric and a reversible color-changing ink formulation bound to the nonwoven fabric. A sanitizer solution is provided, and the nonwoven wipe is impregnated with the sanitizer solution. The surface is wiped with the nonwoven wipe until the color-changing ink formulation changes from a first color indicating sufficient sanitizer solution to a second color indicating insufficient sanitizer solution. The nonwoven wipe is then impregnated with additional sanitizer solution at least until the color-changing ink formulation changes back to the first color.

EXAMPLES

The following reversible color-changing ink compositions were prepared.

| Ingredient | Example 1 Ink | Example 2 Ink |
| --- | --- | --- |
| Bromothymol Blue | 0.3 g | |
| Xylenol Blue | | 0.3 g |
| Cellulose Acetate | 3.7 g | 3.7 g |
| Dibutyl Phthalate | 2.8 g | 2.8 g |
| Stepan 2125M | 0.4 g | 0.4 g |
| Ethylene Glycol | 2.8 g | 2.8 g |
| Acetone | 30 ml | |
| Methyl Ethyl Ketone | | 30 ml |

The ingredients of each ink composition were mixed until the cellulose acetate fully dissolved and all ingredients were incorporated. If necessary, more solvent may be added to achieve desired viscosity. Each ink composition was printed in a pattern on a 24 in×24 in (61 cm×61 cm) nonwoven wipe composed of 80% by weight rayon and 20% by weight polyester fibers. The coated wipe was dried in an oven at 50° C. for 12 hours. The wipe was then rinsed in deionized water to remove any excess ink composition. Each coated wipe was then placed in the following solutions and the following colors were observed.

| Solution | Example 1 Wipe | Example 2 Wipe |
| --- | --- | --- |
| Water | Yellow | Orange-Brown |
| Aqueous QAC Sanitizer (220 ppm) | Green-Blue | Dark Green |

The colors reversed when the wipes initially placed in the aqueous QAC sanitizer were then placed in water, and vice versa. Only slight fading of colors was observed after four cycles, due to some leaching of the ink from the wipes. Most of the ink remained durably bound, as evidenced by the continued reversible color change.

While the embodiments of the invention described herein are exemplary, various modifications and improvements can be made without departing from the spirit and scope of the invention. The scope of the invention is indicated by the appended claims, and all changes that fall within the meaning and range of equivalents are intended to be embraced therein.

We claim:

1. A reversible color-changing sanitizer-indicating nonwoven wipe, comprising:
   a nonwoven fabric; and
   a dried reversible color-changing ink formulation durably bound to the nonwoven fabric by drying using heat and/or vacuum;
   the reversible color-changing ink formulation including about 10-50% by weight of a polymer binder, about 10-50% by weight of a plasticizer, about 10-50% by weight of a wetting agent, and about 1-10% by weight of an anionic indicator compound, based on a dry weight of the ink formulation;
   wherein the reversible color-changing ink formulation causes the nonwoven wipe to repeatedly change back and forth between a first color when a free quaternary ammonium compound in the nonwoven wipe exceeds a threshold concentration and a second color when the free quaternary ammonium compound in the nonwoven wipe falls below the threshold concentration.

2. The nonwoven wipe of claim 1, wherein the nonwoven fabric comprises about 50-100% by weight absorbent nonwoven fibers and about 0-50% by weight reinforcing nonwoven fibers.

3. The nonwoven wipe of claim 2, wherein the absorbent fibers comprise cellulose fibers.

4. The nonwoven wipe of claim 1, wherein the polymer binder comprises a polymer selected from the group consisting of cellulose acetate, cellulose acetate derivatives, carboxymethyl cellulose, ethyl cellulose, nitrocellulose, and combinations thereof.

5. The nonwoven wipe of claim 1, wherein the polymer binder is present at about 20-45% by weight of the ink formulation.

6. The nonwoven wipe of claim 1, wherein the plasticizer comprises a compound selected from the group consisting of dibutyl phthalate, triethyl citrate, bis-(2-butoxyethyl) adipate, bis-(2-ethylhexyl) sebacate, diethyl phthalate, and combinations thereof.

7. The nonwoven wipe of claim 1, wherein the wetting agent comprises a compound selected from the group consisting of ethylene glycol, 2-ethoxy ethanol, triethylene glycol, sorbitol, and combinations thereof.

8. The nonwoven wipe of claim 1, wherein the anionic indicator comprises a compound selected from the group consisting of bromothymol blue, thymol blue, m-cresol purple, xylenol blue, xylenol orange, phenol red, and combinations thereof.

9. The nonwoven wipe of claim 1, further comprising about 1-25% by weight of a particulate inorganic filler.

10. The nonwoven wipe of claim 1, further comprising:
    a sanitizer composition impregnated in the nonwoven wipe which includes a free quaternary ammonium compound.

11. The nonwoven wipe of claim 10, wherein the threshold concentration of free quaternary ammonium compound is about 180-250 ppm based on a dry weight of the nonwoven wipe.

12. The nonwoven wipe of claim 10, wherein the free quaternary ammonium compound comprises a N-alkyl dimethyl benzyl ammonium chloride.

13. The nonwoven wipe of claim 10, wherein the free quaternary ammonium compound comprises a N-alkyl dimethyl ethyl benzyl ammonium chloride.

14. The nonwoven wipe of claim 10, wherein the color-changing ink formulation comprises an anionic indicator compound selected from the group consisting of bromothymol blue, thymol blue, m-cresol purple, xylenol blue, xylenol orange, phenol red, and combinations thereof.

15. The nonwoven wipe of claim 14, wherein the color-changing ink formulation comprises about 20-45% by weight polymer binder, about 15-40% by weight plasticizer, about 15-40% by weight wetting agent, and about 1.5-7% by weight of the anionic indicator compound.

16. The nonwoven wipe of claim 10, wherein the free quaternary ammonium compound comprises a mixture of N-alkyl dimethyl benzyl ammonium chlorides and N-alkyl dimethylethyl benzyl ammonium chlorides.

17. The nonwoven wipe of claim 1, wherein the color-changing ink formulation further comprises an ionic stabilizer.

18. The nonwoven wipe of claim 17, wherein the ionic stabilizer is selected from the group consisting of di(long chain alkyl)dimethyl ammonium chlorides; N-methyl-N,N-bis(long chain alkanoyl oxyethyl)-N-(2-hydroxymethyl) ammonium methylsulfates; vinylbenzyl dimethylcocoammonium chlorides; methyl trioctyl ammonium chlorides; and combinations thereof.

\* \* \* \* \*